United States Patent [19]
Storz

[11] Patent Number: 6,106,456
[45] Date of Patent: Aug. 22, 2000

[54] DEVICE FOR EXAMINING CAVITIES USING AN ENDOSCOPE

[75] Inventor: Karl Storz, deceased, late of Tuttlingen, Germany, Sybill Storz-Reling, executor

[73] Assignee: Karl Storz GmbH & Co. KG, Germany

[21] Appl. No.: 08/732,320

[22] PCT Filed: Feb. 20, 1996

[86] PCT No.: PCT/DE96/00264

§ 371 Date: Nov. 6, 1997

§ 102(e) Date: Nov. 6, 1997

[87] PCT Pub. No.: WO96/25873

PCT Pub. Date: Aug. 29, 1996

[30] Foreign Application Priority Data

Feb. 20, 1995 [DE] Germany .............................. 195 05 774
Feb. 20, 1995 [DE] Germany .............................. 195 05 775

[51] Int. Cl.$^7$ ...................................................... A61B 1/00
[52] U.S. Cl. ............................................ 600/102; 600/174
[58] Field of Search .................................... 600/102, 101, 600/162, 164, 166, 160, 174; 359/404, 409; 403/3; 385/117, 119

[56] References Cited

U.S. PATENT DOCUMENTS

| | | | |
|---|---|---|---|
| 3,064,648 | 12/1962 | Cohen | 600/102 |
| 4,265,561 | 5/1981 | Heckele | 600/102 |
| 4,797,736 | 1/1989 | Kloots et al. | 600/102 |
| 4,819,620 | 4/1989 | Okutsu | 600/114 |
| 5,039,198 | 8/1991 | Van Beek | 385/117 |
| 5,095,887 | 3/1992 | Leon et al. | 600/166 |
| 5,746,693 | 5/1998 | Spitz et al. | 600/162 |

*Primary Examiner*—John P. Leubecker
*Attorney, Agent, or Firm*—St. Onge Steward Johnston & Reens LLC

[57] ABSTRACT

An endoscope assembly for stereoscopic observation of cavities has a head support, an observation system controllably mounted on the support to be aligned with an eye axis of an examining person, and an endoscope with an eyepiece funnel mounted on the head support to be coaxial with and synchronously displaceable with the observation system.

17 Claims, 3 Drawing Sheets

DEVICE FOR EXAMINING CAVITIES USING AN ENDOSCOPE

This application is a continuation of International Application No. PCT/DE96/00264 filed on Feb. 20, 1996 which designated the United States.

DESCRIPTION

1. Technical Field

The present invention relates to a device for examining cavities, in particular, in the bodies of humans and of animals.

2. State of the Art

A device for examining cavities of the type on which the invention is based is known from U.S. Pat. No. 5,039,198.

The known generic device is intended for stereoscopic observation of cavities, in particular, in microsurgery, and is provided with a special endoscope comprising two separate, independent endoscope components. Each endoscope component is provided as practically a complete endoscope and has, in a known manner, a light guide for illumination of the cavity as well as a lens for imaging the object field of the cavity, an image transmitter for the lens image and an eyepiece for observation of the transmitted image. Furthermore, a headband, to which the eyepieces of the two endoscope components are attached in such a manner that the eyepieces are positioned in front of the right respectively the left eye of the examining person, is provided as a head holding means. In order to enlarge the stereo base, the distal ends of the two endoscope components are held on a carrier which maintains the necessary distance of the lenses of the two endoscope components.

However, the carrier impedes the entry of the stereo endoscope into the cavity in which the examination respectively the treatment procedure is to be conducted.

However, above all, due to the use of a special endoscope comprising two separate endoscopes, the device known from U.S. Pat. No. 5,039,198 is very complicated.

The aforementioned drawback ought to be the reason that there is no commercially available device for examining cavities constructed according to U.S. Pat. No. 5,039,198.

Furthermore, holding conventional endoscopes on a mechanical holding means, such as by way of illustration a stand or tripod, in order to have the hands free for the treatment procedure is known. This holding means can be designed in such a manner that it simultaneously offers certain protection against damage to the endoscope and, in particular, to a thin endoscope, by way of illustration due to accidentially coming into contact with the image transmitting component.

However, the known mechanical holding means have the disadvantage that the examining person cannot move his/her head without adjusting the holding means, without losing eye contact with the object of examination.

This is especially the case if the endoscope is an ultra thin endoscope, i.e. an endoscope with a diameter of about 1 to 2 mm or less and with an correspondingly small aperture. Such types of endoscopes are needed for a number of examination procedures in technology or in human respectively in animal bodies.

Ultra thin endoscopes are usually flexible endoscopes, in special cases however, they are fabricated as so-called rigid endoscopes.

In any case, the ultra thin endoscopes have to be handled with extreme care due to their small diameter and therefore only little stability. A holding means for ultra thin endoscopes, which distinctly reduces the risk of damage, is hitherto not known.

DESCRIPTION OF THE INVENTION

The object of the present invention is to provide a device for examining cavities, in particular, in the bodies of humans or of animals using an endoscope, which permits observation of the cavity with normal, conventional endoscopes without using an expensive special endoscope and without the examining person having to hold the endoscope in his/her hand giving the examining person's head a certain amount of freedom of movement without losing eye contact with the eyepiece.

The invented device is provided with a head holding means on which the eyepiece of the, conventionally designed, endoscope is attached in such a manner that it is positioned in front of the eye of the examining person. Due to the head holding means, the endoscope follows the movements of the examining person's head in such a manner that eye contact is not lost in the eyepiece even if the aperture is small.

An element of the present invention is that a single endoscope is provided, the eyepiece funnel of which is connected in a monocular manner to one beam path of the binocular observation system. The apparent drawback of the invented device, notably that observation of the cavity is not possible with both but rather with only one eye is in practice even an advantage:

On the one hand, by way of illustration, physicians are used to view the eyepiece images of endoscopes with only one eye. On the other hand, it permits monocular viewing in the endoscope and with the other eye the surroundings, thus, by way of illustration, to control the incision of the endoscope into the human body without having to "taking the eye off the eyepiece".

Above all, the invented device permits using conventional and, therefore, in most cases available endoscopes.

The head holding means can therefore be designed in a similar or in the same manner as headbands, which are also known as holding means, e.g. for binocular magnifiers from the field of medicine technology, by way of illustration in the ears-nose-and-throat field. In particular, the headband can comprise parts lying close to the forehead and to the rear of the head or a ring-shaped component and an elastic band that is adjustable in length in such a manner that the "headband" can be put on the examining person's head like a "bonnet". However, other designs of the headband are, of course, also possible. With regard to the design of the headbands reference is also made to U.S. Pat. No. 5,039,198.

Furthermore, the head holding means can be designed like eyeglass frames. The head holding means can preferably be designed like so-called measuring eyeglass frames like those used, by way of illustration, by opticians for subjective refraction determination. Measuring eyeglass frames, notably, permit easy adjustment to a great variety of head shapes and are, moreover, designed to hold relatively heavy parts without becoming uncomforatable for the eyeglass wearer or the measuring eyeglasses slipping on the ridge of the nose. In particular, eyeglass frames of this type can be easily adjusted by altering the bridge distance, the length of the sides of the frames, the support areas on the ridge of the nose, etc. to various users in such a manner that the invented device can be employed by a great variety of users.

In view of the fact that a number of manufacturers offer measuring eyeglass frames, it is not necessary to go into detail on their exact design here. The use of other eyeglass frames is, of course, also possible.

Fundamentally, for the present invention regarding the design of the head holding means, it is only important that it permits secure, non-slipping wearing by the examining person.

In an especially preferred embodiment of the present invention, an observation system is attached to the head holding means. This observation system magnifies the eyepiece image for the examining person. The eyepiece funnel of the endoscope for this purpose is connected to the one beam path of the observation system in a monocular manner in such a way that the eyepiece image is magnified for the examining person. This magnification of the eyepiece image is especially advantageous, because the eyepiece image, by way of illustration, of ultra thin endoscopes is small compared to normal endoscopes.

The observation system can, by way of illustration, be eyeglass frames having, for magnification of the eyepiece image and/or for correction of aberrations, suited lenses, a binocular magnifier or a telescope and, in particular, a prism telescope whose intercept distance is matched to the respective application.

Any known binocular magnifier, such as those, by way of illustration, used in the field of medical technology, can be employed as the binocular magnifier.

Which observation system is to be employed is, i.a. dependent on the respective application and/or the needed magnification of the eyepiece image:

The "cumulated" magnification of the observation device and of the endoscope is sufficient for carrying out complicated surgery in such a manner that use of an invented device frequently obviates the use of a surgical microscope, which is much more expense than a binocular magnifier respectively a corresponding telescope. The use of a telescope respectively a binocular magnifier has the particular advantage that not only the surroundings but also the eyepiece image is greatly magnified. In this way, even microsurgery can be carried out using an endoscope for observation.

By way of illustration, when conducting eye surgery, magnification by a binocular magnifier or by a telescope is fully sufficient for examining the eye and, in particular, the surroundings of the incision of the endoscope during the examination respectively treatment procedure. On the other hand, operation of the telescope respectively of a binocular magnifier is practically confined to setting the pupil distance and the object field to be observed. In comparison, operating a surgical microscope is very complicated.

Use of eyeglass frames, by way of illustration, permits providing the lens ring, which is not connected to the eyepiece funnel of the endoscope via a coupling, with a lens having no optical effect or with a lens that has an optical effect (spherical and cylindrical effect), which corrects the aberration of the examining person for observation of the surroundings, in particular, taking into account the respective "operating distance". However, the ophthalmic lens through which one looks in the eyepiece can, of course, also be provided, in addition to the magnifying effect, with an ability to correct aberrations while taking into account the operating distance in the observation of the eyepiece image. Using eyeglass frames has the advantage, as already mentioned, that relatively inexpensive glass frames are commercially available which, adapting well to the physiognomy of the respective examining person, excellently compensate the weight.

The easing of the weight is improved by the eyepiece component of the endoscope being supported on the ridge of the examining person's nose. For this purpose, it is preferred if the eyepiece component of the endoscope is connected to the observation system via a beam deflection element which deflects the beam path 90°.

Supporting the eyepiece component can, by way of illustration, occur using a modified nose saddle attached to the eyeglass frames and by the saddle being provided with a holding means for the eyepiece component.

The connection between the eyepiece of the endoscope and the (monocular) beam path of the respective observation system provided may be of a great variety of types:

By way of illustration, the eyepiece can be connected to the observation system without interposing an optical system, by way of illustration, a dish-shaped coupling like those employed for flange-mounting video cameras to endoscopes. This coupling can be designed in such a manner that the eyepiece funnel can be turned in relation to the observation system when it is in a coupled state.

Furthermore, the eyepiece can be connected to the observation system via a link optic. Link optics of this type are known in the field of endoscopy, by way of illustration, from DE 25 07 346 C2, obviating going into more detail here about the design of this type of optics. The connection between the eyepiece and the link optic as well as between the link optic and the observation system can again occur in the known manner.

By using a link optic, the observation optic can be moved to and fro without the endoscope moving with it or without losing the view in the eyepiece. In another preferred embodiment of the present invention, a spirally shaped tube surrounds the link optic. In this event, the light guide cable respectively cables can be led inside the spirally shaped tube.

Instead of or in addition to the link optic, an optical system can be provided which permits, by way of illustration, by swinging in a deflection prism into the beam path in front of one or both exit apertures, enabling switching between binocular observation of the surroundings and (monocular) observation of the eyepiece image of the endoscope. With this arrangement, binocular viewing into the eyepiece of the endoscope can also be realized by means of a suited beam splitter, because due to the swinging out of one or both deflection prisms, it is still possible to observe the surroundings of the incision with one or both beam paths of the magnifier.

Preferably the head carrier provided according to the present invention can be used as a carrier of additional respectively supplementary devices:

For instance, an illumination device, which illuminates the surroundings, can be attached to the headband, to the eyeglass frames and/or to the observation system. In this way, the examining person can observe with one eye the cavity into which the endoscope is inserted. Without having to remove the headband with the attached endoscope, the examining person can inspect the surroundings, by way of illustration the "incision" of the endoscope into the human or animal body. If a binocular observation system is employed, this illumination device can be disposed, in particular, between the two beam paths of the observation system.

As already mentioned, the headband can also be used as the carrier of additional devices:

Therefore, it is preferred if the light guide cable for the ultra thin endoscope and/or the light guide for the illumination device are led on the head carrier. In this way it is ensured that the operating person does not get "tangled" in the cables.

The use of a head carrier has hitherto not been considered for ultra thin endoscopes apparently, because these endoscopes have a tendency to break. Tests by the inventor have, however, shown that there is substantially less danger of damaging the endoscope if it is attached to a head carrier than if a rigid mechanical holding means, which is positioned independent of the examining person, is used.

As already explained, ultra thin endoscopes are usually flexible endoscopes. As these endoscopes have a tendency to break and therefore have to be handled with extreme care, in a preferred embodiment of the present invention, a protective tube is provided for the endoscope, out which the endoscope can be drawn. In another embodiment of the present invention, this protective tube can be attached to the clothing of the examining person, by way of illustration using a clamp. This protective tube which can, in particular, be designed spiral-shaped, protects the endoscope when not in use. As it is only drawn out of the protective tube as far as the respective examining procedure requires, the risk of damaging the ultra thin endoscope is reduced to a minimum. Furthermore, the endoscope does not "sag"; this is especially troublesome in handling ultra thin endoscopes and is frequently the cause of damage.

In addition to using a head carrier, the observation device can, of course, be "put on a stand" in the same manner as a surgical microscope if the head carrier is briefly in the way.

As already explained, the invented device can be universally utilized both in technological as in medical fields. The endoscope can be guided in a known manner in a shaft. This shaft cannot only be provided with a channel for a surgical instrument, but also can be used for guiding an additional light guide, which illuminates the object field.

In the medical field, there are not only possible applications in minimal-invasive surgery or microsurgery, but also in eye examinations and carrying out eye surgery on human or animal eyes. In the examination respectively the surgery, the endoscope is introduced immediately next to the eye, by way of illustration positioned in the region of the tear bag or in the eye such as by way of illustration into the vitreous body of the eye. As is customary in endoscopic examinations, an observation device is provided, the light of which is coupled into a light guide disposed in the endoscope, which illuminates the object field of the endoscope lens.

In eye surgery it is preferred if an illumination device, which illuminates the eye to be examined, is disposed on the headband or on the binocular magnifier respectively on the telescope. In this way, the examining person can observe with one eye the eye to be examined respectively treated, at which the endoscope is disposed respectively in which the endoscope is inserted. Without having to remove the endoscope, the examining person can inspect the surroundings, by way of illustration, the "incision" of the endoscope into they eye or another region of the eye. The illumination device can be disposed between the two beam paths of the binocular magnifier in such a manner that in binocular observation of the eye the object field can be fully illuminated without a flange-mounted endoscope.

BRIEF DESCRIPTION OF THE DRAWING

The present invention is made more apparent in the following by way of example without the intention of limiting the scope or spirit of the overall inventive idea using preferred embodiments with reference to the accompanying drawing.

DESCRIPTION OF PREFERRED EMBODIMENTS

Figure 1:
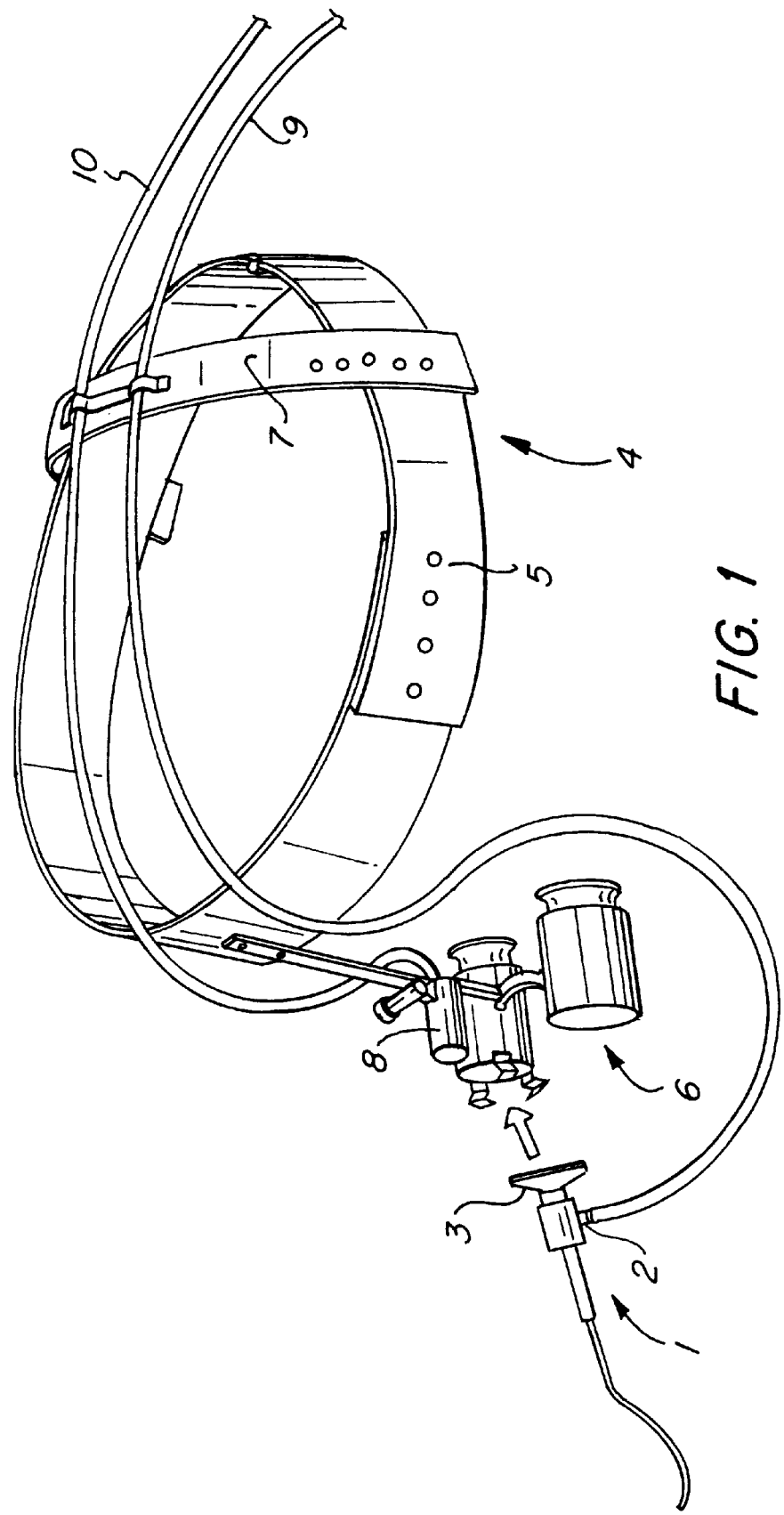
FIG. 1 shows a schematic perspective view of a first preferred embodiment of the present invention.

FIG. 1 shows a first preferred embodiment of an invented device for examining cavities, in particular, in human or animal bodies.

A component of the invented device is an ultra thin endoscope 1 provided with a light guide, which is not depicted in detail, having a light guide connection 2 as well as a lens at the, not depicted, distal end. The image generated by the lens is led by an image transmitted to the proximal end of the endoscope shown in FIG. 1 in such a manner that it can be observed through an eyepiece 3.

In the shown preferred embodiment, the endoscope 1 is a flexible endoscope; accordingly the image transmitter preferably comprises an ordered glass fiber bundle.

An element of the preferred embodiment is that a headband 4 is provided comprising in an as such known manner a ring-shaped component 5 and a holding band 7. The diameter of the ring-shaped component 5 and the length of the headband 7 are adjustable. However, other embodiments are, of course, also possible.

Attached to the headband 4 is an as such known binocular magnifier 6 having the usual possible adjustments for inclining, pupil distance and, if need be, focussing. One beam path of the binocular magnifier 6, in the depicted preferred embodiment the right view as seen from the headband wearer, is provided on the side facing away from the observation with a coupling which permits flange-mounting of the eyepiece funnel 3 of the ultra thin endoscope 1. For this coupling, types of coupling like those known by way of illustration for flange-mounting endoscopes to video cameras can be employed. In this way, the eyepiece is not only positioned in front of the eye of the headband wearer and follows every movement of the head without the headband wearer having to hold the endoscope respectively if using a conventional holding device having to continuously readjust the holding device, but also magnifies the eyepiece image. This not only facilitates observation of the very small eyepiece image of the ultra thin endoscope, but also in many cases obviates additional respectively supplementary use of a surgical microscope.

Furthermore, the headband can be used to hold an illumination device 8 which illuminates the surroundings. The illumination device 8 which is provided with a condenser lens, which is not depicted in detail, is disposed between the left and right beam path of the binocular magnifier 6.

Light guides 9 and 10 led on the headband 4 and, in particular, on the holding band 7 via suited holding means are provided for supplying the light of the light guide to the endoscope and to the illumination device.

Figure 2:
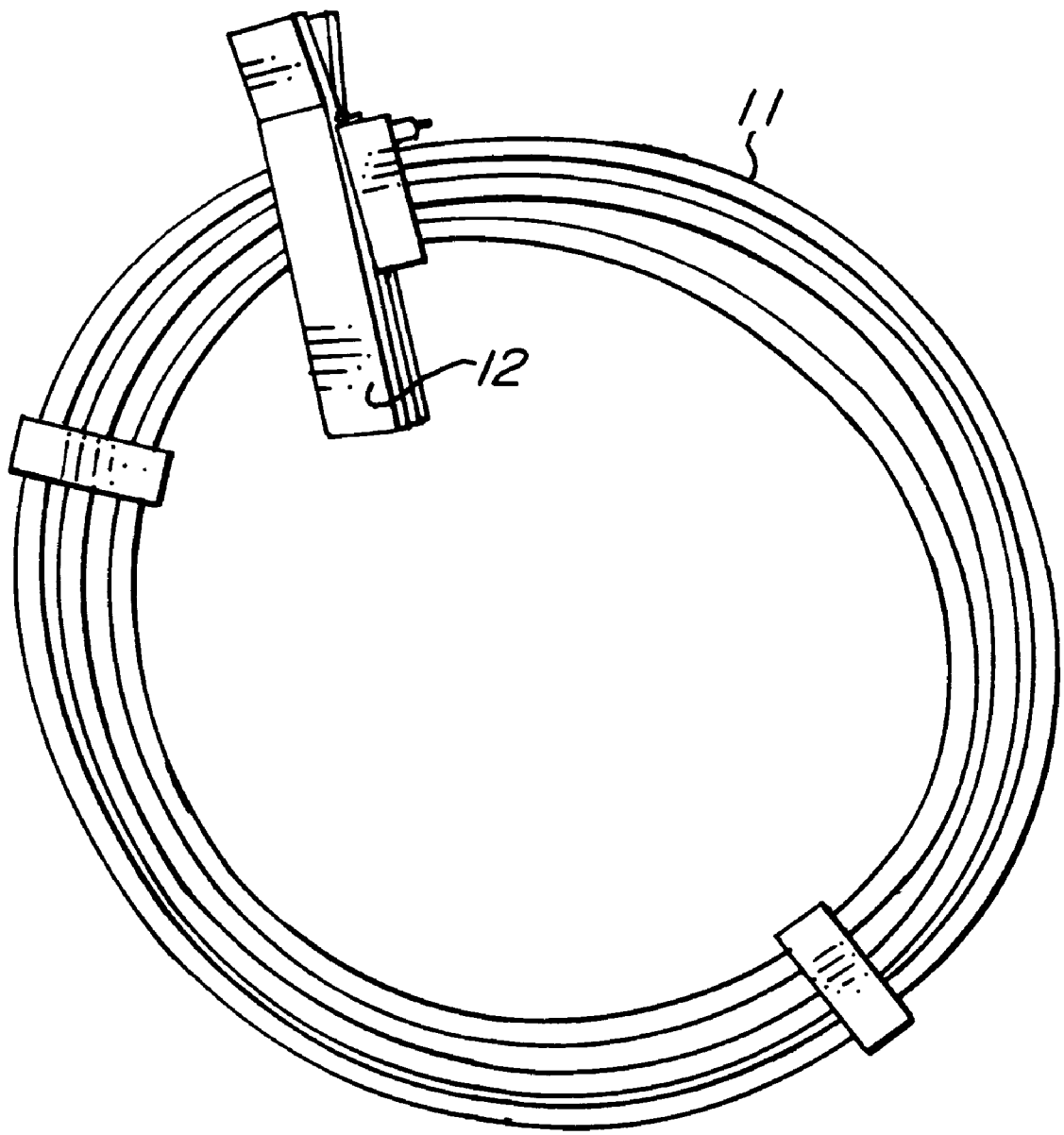
FIG. 2 shows an invented optionally provided protective tube.

FIG. 2 shows a protective tube 11 for the endoscope 1 out of which the flexible endoscope can be drawn. The protective tube 11 is designed spiral-shaped. Furthermore, a clamp 12 is provided with which the protective tube can be attached to the clothing of the examining person.

As the ultra thin endoscope 1 is drawn out of the protective tube 11 only so far as required for the respective examination procedure, the risk of damaging the ultra thin endoscope is reduced to a minimum. Moreover, the endoscope does not "sag"; this sagging is especially troublesome in handling the ultra thin endocscopes and is often a source of damage.

A great variety of modifications compared to the preferred embodiment depicted in FIG. 1 are, of course, also possible within the scope of the present invention:

Therefore, the headband can be designed in a different manner than as shown in the drawing. A different head carrier can also be employed instead of a headband.

Figure 3:
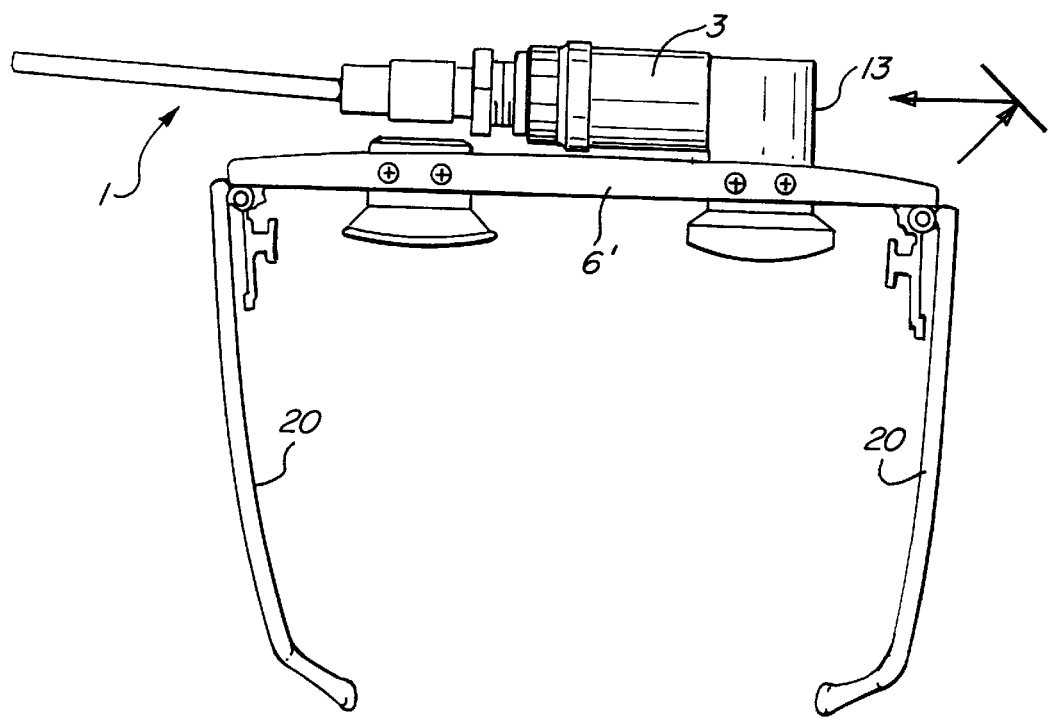
FIG. 3 shows a second preferred embodiment of the present invention.

A corresponding possibility is shown in FIG. 3: in the second preferred embodiment shown in this figure, a pair of eyeglasses 6' respectively "eyeglasslike" frames having frame sides 20 are used instead of the binocular magnifier 8 as the observation unit. Moreover, in this preferred embodiment, the eyepiece 3 of endoscope 1 is not directly attached to the lens ring of the eyeglass frames, i.e. the exit aperture of the observation unit 6', but due to the use of a deflection prism 13 is disposed offset and at an angle of 90°. The eyepiece of the endoscope 1 is supported on the ridge of the examining person's nose.

Figure 4:
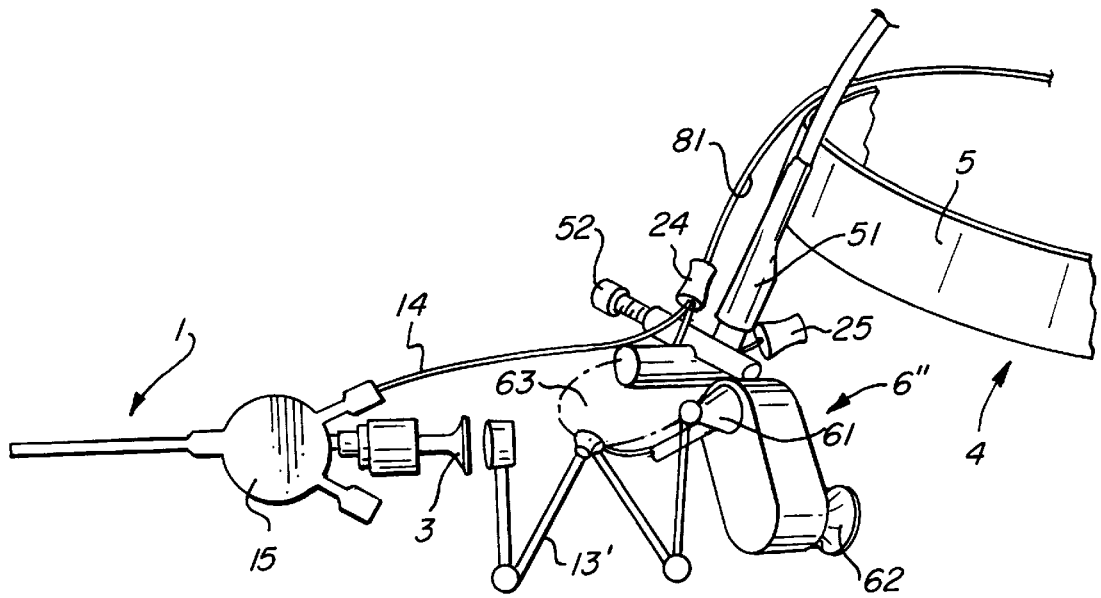
FIG. 4 shows a third preferred embodiment of the present invention.

FIG. 4 shows an invented device for examining the eye as well as for conducting eye surgery. The device is provided with an endoscope 1, which can be positioned next to an eye, which is not shown, or can be introduced into the interior of the eye. Furthermore, a observation device, which is separate from the endoscope 1, is provided. In the depicted preferred embodiment, the observation device is a prism telescope 6".

The eyepiece funnel 3 of the endoscope 1 is connected via a link optic 13' to a view opening 61 of the telescope 6". In this way, the eyepiece image of the endoscope can be observed enlarged through the eyepiece 62 of the telescope 6" allocated to the view aperture 61.

An illumination device 8, which illuminates the surroundings which can be observed through the other beam path of the prism telescope 6", is provided between the two parts of the binocular prism telescope 6". The second beam path is schematically designated 63.

Furthermore, a not depicted light source, the light of which is coupled via a light guide 81 into the illumination device 8, is provided. Moreover, the light of the light source is coupled into a thin light guide 14, the purpose of which is to illuminate the view field of the endoscope. The light guide 81 is led through a guide 24 on the prism telescope 6". The purpose of another guide 25 is to hold another light guide or a thin flexible endoscope.

The endoscope 1 is led in an as such known manner in a shaft 15 in which the light guide 14 is guided.

The shaft 15 can be provided with one or several channels for surgical instruments.

The prism telescope 6" is attached to a headband 5 via a holding means 51 and an adjustment screw 52 to adjust to inclination.

Compared to the aforedescribed preferred embodiments, a great variety of modifications and alterations within the scope of the present invention are, of course, also possible.

Instead of monocular coupling of the endoscope, binocular observation into the eyepiece 3 of the endoscope 1 can also be realized via a beam splitter. However, in that case observation of the surroundings is not possible without disconnecting the connection to at least one exit aperture of the binocular magnifier. Alternatively the endoscope can also be disposed not directly at the exit aperture of the magnifier but off set and at an angle. The beam path of one or of both viewing points of the observation system, such as the binocular magnifier can then be deflected by one respectively two pivotable deflection prisms before the exit aperture(s) in such a manner that instead of the surroundings, the eyepiece image can be observed through the magnifier. Binocular observation of the eyepiece image, of course, requires the use of a fusion prism or the like.

The binocular observation unit provided according to the present invention for observation of the eyepiece image of an endoscope and, in addition, for observation of the surroundings can, of course, also be employed to observe the eyepiece images of endoscopes, which are not ultra thin in the aforedescribed sense, thus by way of illustration of rigid endoscopes which have a diameter of 4 mm.

What is claimed is:

1. A head mounted device for examining cavities in the bodies of humans or of animals, said device having:

an endoscope provided with a light guide for illumination of a cavity, a lens, an image transmitter for an image generated by said lens and an eyepiece for observation of said transmitted image, the eyepiece having an eyepiece funnel, a head holder, an observation system having an optical axis and being attached to said head holder, and a linked optical system connecting the eyepiece funnel to said observation system in a monocular manner, so as to enable the eyepiece and the observation system to be synchronously displaced in a direction transverse to the optical axis in response to a movement of the head of the examining person.

2. The device according to claim 1, characterized by said observation system magnifying said image for the examining person.

3. The device according to claim 1, characterized by said observation system being a binocular observation system, said binocular observation system being selected from the group consisting of eyeglass frames with suited lenses, a binocular magnifier, a telescope, and a prism telescope.

4. The device according to claim 3, wherein said observation system comprises eyeglass frames having opposite sides, said opposite sides forming said head holder.

5. The device according to claim 1, characterized by said head holder being provided with a headband.

6. The device according to claim 1, characterized by a spirally shaped tube surrounding said linked optical system.

7. The device according to claim 6, characterized by at least one light guide cable being guided in said spirally shaped tube for illuminating the surroundings.

8. The device according to claim 1, wherein said holder further comprising an illuminating device, which illuminates the surroundings, said illuminating device being attached to said head holder.

9. The device according to claim 8, wherein the observation system has two beam paths, said illuminating device being attached to said holder between the two beam paths.

10. The device according to claim 8, characterized by said illuminating device being provided with a second light guide connecting illuminating device to a light source.

11. The device according to claim 10, characterized by said light guide for said illuminating device being attached to the head holder or on a head band.

12. An endoscope according claim 1, characterized by a light guide cable, which couples the light from said illumination device into the light guide in said endoscope, being led on said observation system and/or on the head holder.

13. A device according to claim 12, characterized by said endoscope being a flexible endoscope.

14. The device according to claim 1, wherein said endoscope has a shaft.

15. A device according to claim 14, characterized by an additional light guide for illuminating the object field of the endoscope being attached to said shaft.

16. A device according to claim 15, characterized by at least one channel for a surgical instrument being provided in said shaft.

17. A device according to claim 2, characterized by said shaft being a protective tube for said endoscope, out of which said endoscope can be drawn.

* * * * *